US009959387B2

(12) United States Patent
Liguori et al.

(10) Patent No.: US 9,959,387 B2
(45) Date of Patent: May 1, 2018

(54) METHOD FOR TRACKING SANITARY MATERIALS AND GOODS WITH RFID IDENTIFICATION SYSTEM; CONTAINMENT AREA AND/OR STRUCTURE ACTUATING SAID METHOD

(71) Applicant: INGEGNERIA BIOMEDICA SANTA LUCIA S.P.A., Gragnano Trebbiense (IT)

(72) Inventors: Pierangelo Liguori, Gragnano Trebbiense (IT); Giorgio Pavesi, Gragnano Trebbiense (IT); Fulvio Rudello, Gragnano Trebbiense (IT)

(73) Assignee: SANTA LUCIA PHARMA APPS S.R.L., Gragnano Trebbiense (IT)

( * ) Notice: Subject to any disclaimer, the term of this patent is extended or adjusted under 35 U.S.C. 154(b) by 0 days. days.

(21) Appl. No.: 14/765,976

(22) PCT Filed: Feb. 4, 2014

(86) PCT No.: PCT/IB2014/058782
§ 371 (c)(1),
(2) Date: Aug. 5, 2015

(87) PCT Pub. No.: WO2014/122578
PCT Pub. Date: Aug. 14, 2014

(65) Prior Publication Data
US 2015/0379216 A1   Dec. 31, 2015

(30) Foreign Application Priority Data
Feb. 5, 2013 (IT) .............................. PR2013A0007

(51) Int. Cl.
*G06F 19/00* (2011.01)
*G06Q 10/08* (2012.01)
*G06K 7/10* (2006.01)

(52) U.S. Cl.
CPC ....... *G06F 19/327* (2013.01); *G06K 7/10346* (2013.01); *G06Q 10/08* (2013.01)

(58) Field of Classification Search
CPC ........................... G06Q 10/087; H04W 4/008
(Continued)

(56) References Cited

U.S. PATENT DOCUMENTS

| 8,362,878 B2* | 1/2013 | Molewyk | ................ D06F 93/00 |
| | | | 312/211 |
| 2002/0063622 A1* | 5/2002 | Armstrong | ........... G06K 7/0008 |
| | | | 340/10.31 |

(Continued)

*Primary Examiner* — Vernal Brown
(74) *Attorney, Agent, or Firm* — Young & Thompson

(57) ABSTRACT

Method for tracking sanitary materials and goods with a RFId identification system; the materials and goods provided with at least one label containing a microchip containing data of the material or good and an antenna; the materials and goods placeable in a storage area provided with a plurality of transceiving radio frequency identification antennae and associated connectivity devices; the plurality of antennae and connectivity devices placed so as to receive and exchange information via RFId technology inside the set area, so as to automatically record and detect the loading and/or collecting of the labeled materials and goods and exchange information relative to the identified objects; the method includes: a) carrying out the exchange of tag-antenna information in a range of radiofrequencies comprised between 850 and 960 MHz (UHF); and b) restricting the range of radiofrequencies (UHF) through the shielding of the area arranged for storage of the materials and goods.

11 Claims, 2 Drawing Sheets

(58) Field of Classification Search
USPC .......................................................... 340/10.1
See application file for complete search history.

(56) References Cited

U.S. PATENT DOCUMENTS

| | | | |
|---|---|---|---|
| 2005/0088284 A1* | 4/2005 | Zai | G06K 7/10356 340/10.2 |
| 2006/0290472 A1* | 12/2006 | Onderko | G06K 7/0008 340/10.1 |
| 2009/0117855 A1* | 5/2009 | Rofougaran | H01L 23/66 455/73 |
| 2011/0248828 A1* | 10/2011 | Margalef | G06K 19/07749 340/10.1 |
| 2014/0035731 A1* | 2/2014 | Chan | G06K 7/10356 340/10.3 |

* cited by examiner

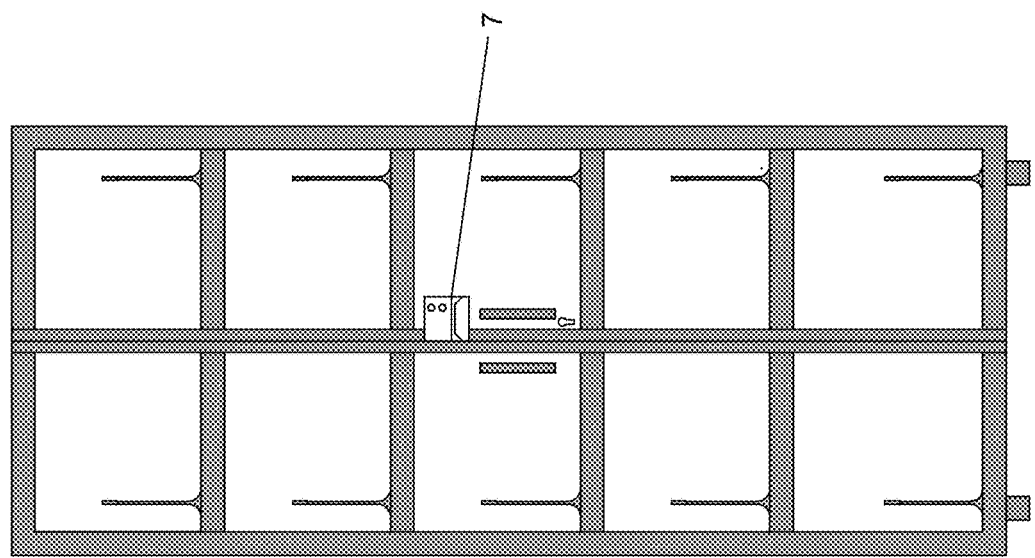
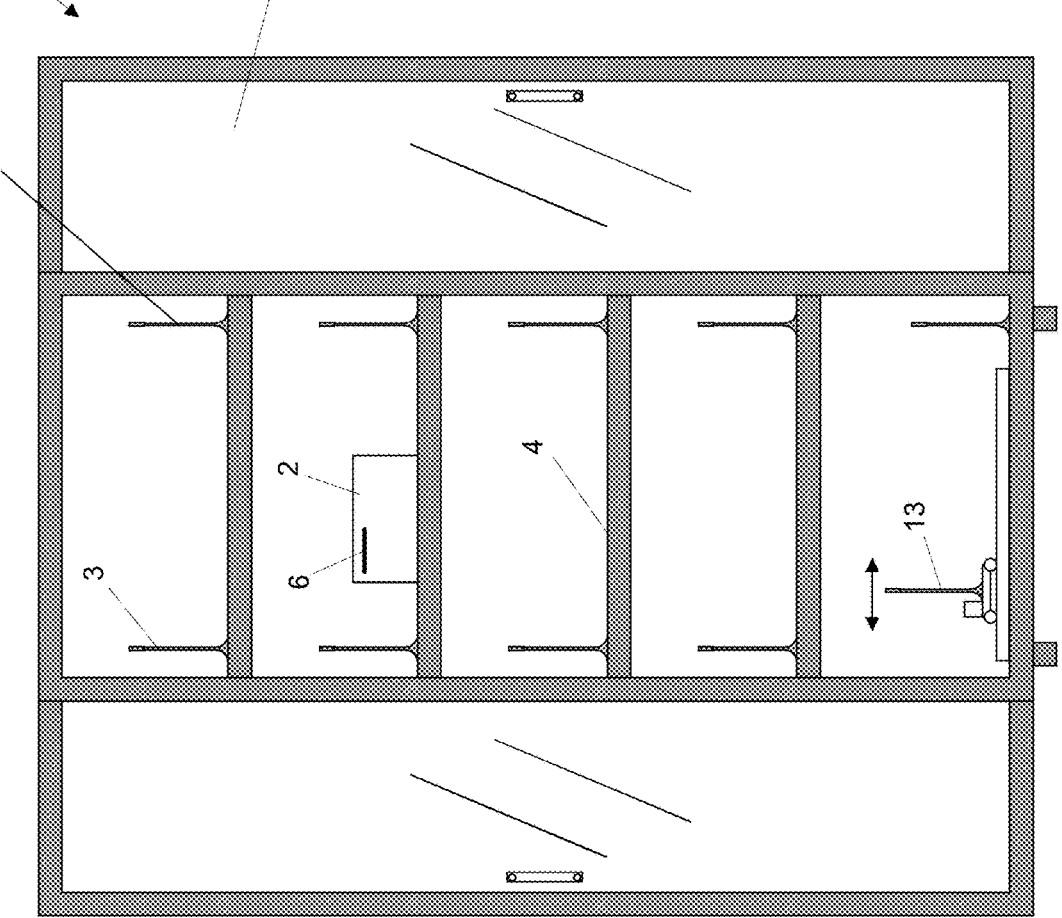

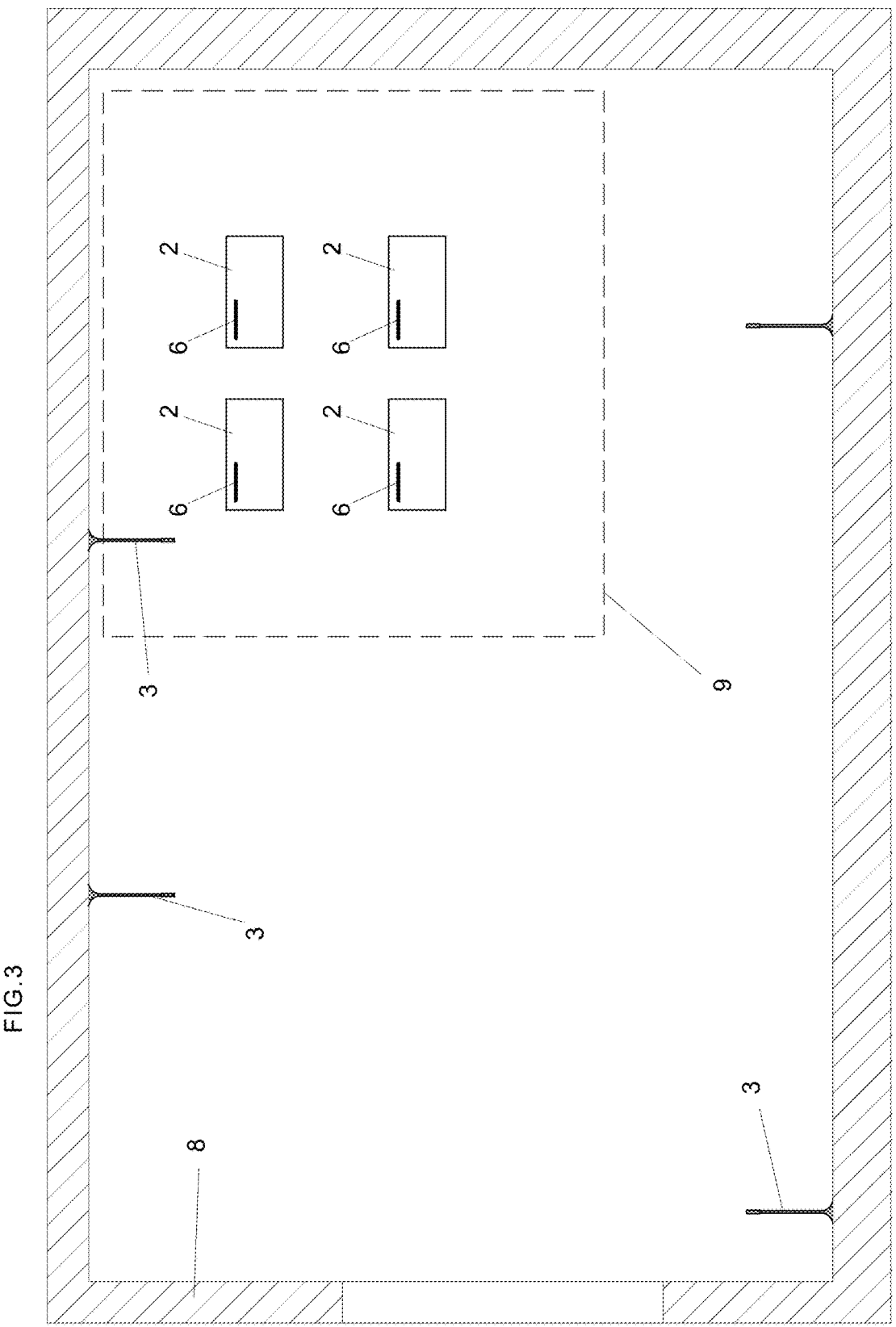

METHOD FOR TRACKING SANITARY MATERIALS AND GOODS WITH RFID IDENTIFICATION SYSTEM; CONTAINMENT AREA AND/OR STRUCTURE ACTUATING SAID METHOD

FIELD OF APPLICATION OF THE INVENTION

The following form the object of the finding:
A method for tracking sanitary materials and goods with radio frequency identification system, also known with the acronym RFId;
The containment area and/or structure with which the aforesaid method is actuated for tracking sanitary materials and goods.

By 'sanitary goods' it is intended those products which, due to their diffusion, functions and in many cases economic value, have considerable importance in the activity of hospital/medical structures.

Included among the materials and sanitary goods are medical devices, drugs, biological tissues and cells: all form an important part of the hospital economy and are critical from an organizational standpoint. In other words, they represent an area of strong interest from a clinical and economical standpoint, such that the availability of suitable management instruments takes on considerable importance.

With reference to the definitions employed, 'medical device' defines any instrument, apparatus, plant, substance or another product, used on its own or in combination, including the computer software employed for the correct operation thereof, intended to be employed for the purpose of:
diagnosis, prevention, control, treatment or attenuation of a disease;
diagnosis, control, treatment, attenuation or compensation of an injury or a handicap;
study, substitution or modification of the anatomy or a physiological process;
conception operation,
whose main action is not attained with pharmacological or immunological means nor via metabolic action, but whose function can be assisted by such means.

'Drug' defines:
1) any substance or association of substances presented as having curative or prophylactic properties for human diseases;
2) any substance or association of substances used or administered for the purpose of restoring, correcting or modifying physiological functions, by exerting a pharmacological, immunological or metabolic action, i.e. for establishing a medical diagnosis.

A 'tissue' is defined as a set of structurally similar cells, associated by function, used for tissue engineering treatment and/or research purposes.

A 'cell' is defined as single human cells or a set of cells not connected by any form of connective tissue, used for transplant purposes and/or research.

From the tests conducted, in particular in the context of management of the goods/devices, it emerged that the most significant from the clinical criticality and/or economical standpoint can be mainly summarized in the following types: prosthetic material, pacemakers and valves, ocular prostheses, catheters for diagnostic operation, high-cost suture material, surgical instrumentation and kits.

It resulted from the analysis that, with regard to millions of goods/medical devices used annually in an average-size hospital/medical structure, a percentage of approximately 1%-3% of medical devices—more significant in terms of clinical criticality and costs—has a cost that reaches nearly 80% of the total cost.

It can thus be observed that, even considering the natural intercompany variability, with the present tracking process of a very limited percentage of the overall number of devices used by the company/hospital, it is possible to track and keep monitored—even tracing the consumption to the specific patient—approximately 80% of the annual consumption value.

From that stated above, it follows that it is of interest to have a secure storage and tracking of the critical goods, which allows monitoring and recording the entire path of a single item used within the hospital structure, in all steps thereof—whether such item is a sanitary good, a medical device or a drug—from the point of entry in the hospital/medical structure to the single final user patient. Indeed, if the tracking from the producer/supplier to the hospital/medical structure, generally in its own pharmacy, is assured by current regulations and by quality procedures relative to the supply and provisioning modes, the planning, control and tracking from the pharmacy to the patient are not ensured by regulated and secure structured procedures.

PRIOR ART

With the term 'RFId' (acronym of Radio Frequency Identification), a technology is indicated for the automatic identification of objects, animals or people based on the capacity to store and access data by using RFId labels or transponders or tags.

The devices described hereinbelow and the tracking process is based on the remote reading of information contained in an RFId tag by using RFId tag readers or connectivity devices.

There are two large classes of RFId technologies, divided according to the different energy source that powers them:
1) Passive RFId Technologies; the "Passive" Tags receive the energy necessary for operating, exclusively from the RF field supplied by the system. The communication between Tag label and connectivity device only occurs inside the electromagnetic field.
2) Active RFId Technologies; the "Active" Tags instead have their own power supply, normally constituted by a long-duration battery. When interrogated by the "reading system", they emit their own RF energy that can be propagated over much greater distances.

Within the above-indicated classes, there are two further subdivisions:
3) Semi-Passive RFId Technologies; the Semi-"Passive" Tags communicate with the Reader when they are inside the RF (HF or UHF) field. They are equipped with a micro-battery (made of paper or organic material) used for supporting the communication with sensors (e.g. temperature, humidity sensors, etc.).
4) Semi-Active RFId Technologies; the Semi-"Active" Tags communicate with the Reader when they are affected by the RF (HF or UHF) field. They are equipped with a micro-battery used for supporting the communication with the Reader and also communicate outside the RF field.

An RFId tag is constituted at least by a microchip capable of containing data (including a number, generally unique) and by an antenna.

The main distinctive element of RFId technology is the frequency; as a function of the frequency range used, the following three categories can be identified:

1. LF (Low Frequency): typically 119-135 KHz, coupling by means of inductive magnetic field. Maximum communication distance less than 80 cm. Data transfer rate: 2-4 Kbit/s. Tag size (attained with spiral antenna): 2 mm minimum diameter. Memory capacity: read only. Transit speed allowed: 0-10 Km/h.
2. HF (High Frequency): typically 13.56 MHz, coupling by means of inductive magnetic field. Maximum communication distance less than 150 cm. Data transfer rate: 28 Kbit/s. Tag size (attained with loop antenna): 10 mm minimum diameter, maximum format A5. Memory capacity: from 64 bit to 4 Kbyte. Transit speed allowed: 0-30 Km/h.
3. UHF (Ultra High Frequency): typically ranging from 850 to 960 MHz, coupling by means of electromagnetic field. Maximum communication distance greater than 11 m. Data transfer rate: from 40 to 320 Kbit/s. Tag size (attained with dipole antenna): 10 mm minimum diameter, maximum format A5. Memory capacity: from 64 bit to 1024 bit. Transit speed allowed: 0-70 Km/h.

The HF and UHF technologies are provided with "anti-collision function" that allows the massive detection of Tags at the same time instant.

One of the main difficulties that are encountered in the management of the tracking, with method based on RFId tag, is to guarantee the effectiveness in the automatic detection of the devices to be tracked.

Each of the abovementioned technologies has specific characteristics. The selection of the most suitable RFId technology depends on various elements:
  environmental factor: it must be able to be applied in a manner so as to ensure the success of its use and/or operation;
  functional factor: it must not limit and/or complicate current operations;
  economical factor: it must be economically sustainable.

In consideration of the abovementioned factors, and having as reference the range of technological characteristics available today, the use of the RFId technology has known limits that lead to the failure of the Tag reading, which in the current case would lead to ineffectiveness in the automatic detection of the devices to be detected.

The main sources of error are the following:
  devices which, due to the particular content of metal or liquid parts, can generate incorrect detections due to the interference that these metal or liquid parts generate with the electromagnetic waves used;
  devices which, due to the particular physical form of the containers, during the storage on shelves/cases generate a positioning that places the RFId tags very close together, which makes it difficult to correctly identify all the single stored devices;
  the particular form of the electromagnetic field which is generated in the interactions with RFId tag and in general is such to generate detections that even go beyond the storage zone, thus risking detecting other interaction sources and/or other RFId tags that belong to other storage zones;
  geometric constraints: obligation of placing the objects according to a particular geometric arrangement and oriented in a manner so as to obtain the correct coupling of the RF radiation with the tag (only in the case of use of the LF and HF technology);
  transceiving antennae: in the presence of metal surfaces, the LF and HF antennae must be suitably configured and spaced from the metal. The UHF antennae may also be positioned close to metal surfaces.

In analogous solutions, the use of HF technology is proposed, easily manageable for the reduced radius of action (about 150 cm) which is naturally limited to restricted settings, which does not risk detecting objects situated far away and which does not generate interference with other objects placed far away. However, this technology does not allow precision and accuracy in the automatic detection of the objects of interest, mainly for the above-described limits, i.e.:
  the constraining condition of the arrangement of the Tag, applied to the sanitary good, with respect to the transceiving antennae,
  the impossibility of reading in the presence of metal material.

Description and Advantages of the Finding

The object of the present finding is to provide the art with a method for tracking materials and sanitary goods and/or medical devices with RFId technology and, in particular, using UHF technology, which does not set constraints on the orientation of the Tags and offers a good reading capacity even in the presence of metal materials and/or liquids.

Since the UHF technology has a reading capacity extended over a dozen meters from the transceiving antennae, in order to render the automatic detection of the goods/devices to be tracked effective and correct, the finding provides for actuating a series of technological and procedural expedients that allow detecting with certainty all the devices and only those contained in the storage zone, excluding those devices placed in adjacent storage zones.

In brief, among the first expedients of the finding, the fact of providing for the following is underlined:
  a. carrying out the exchange of tag-antenna information in a range of radiofrequencies comprised between 850 and 960 MHz (UHF);
  b. restricting the range of radiofrequencies (UHF) through the shielding of the area arranged for storage of the materials and goods.

Other expedients, implemented in order to ensure the maximum reliability of the tag applied to the sanitary materials and goods, provide that the exchange of information in the radiofrequency (UHF) field occurs by not turning on, at the same time, the entire plurality (P) of antennae arranged in the area set for the storage of the materials and goods, but rather operating such that only a part is operative, exciting the RFId tag.

In addition, it is provided to vary both the field and the polarization of each antenna, setting the stay tempo in each obtainable combination.

Further object of the present finding is to protect the structure obtained by the described tracking method. Once the most critical goods have been determined—most critical from an economical or clinical-sanitary standpoint—it is provided to identify particular areas of wards/departments in which the storage thereof is managed. The organization provides for the positioning of an apparatus, such as a cabinet or closed containment structure, equipped with antennae and readers based on RFId technology (acronym of Radio Frequency Identification), or the attainment of a room set as storage site, it too equipped with RFId technology. By means of said RFId devices, the management process detects the loading and/or collecting of said goods equipped with RFId tag and interacts with the information system in order to exchange information relative to the identified objects.

A further management variant is attained through the delimiting of the storage area site with suitable physical barriers, which are associated with a series of antennae and identification devices based on RFId technology, capable of detecting the entry and/or exit of the devices equipped with RFId tag.

Naturally, for the method to be actuatable, the materials and/or sanitary/medical devices must be provided with an integrated circuit—whose communication is managed in radiofrequency—containing the data of the device, and with an antenna.

The labeling and encoding of the goods/medical devices will be carried out by applying, on the package of the good/device, a label containing one or more RFId labels or tags. Alternatively, the labeling and encoding will occur directly on the good/device, by applying one or more RFId tags.

The labeling provides to identify the goods/devices through a series of information adapted to unequivocally recognize the good/device in the tracking path. The information is written in the RFId tag and partly also on the label itself, in a manner so as to be able to identify it even manually if, in the tracking path, there is a problem on the reading of the RFId tag. An example of the main identification information is represented by the following list of information:
 description
 producer code
 CND code
 CND description
 inventory code
 inventory description
 EAN code
 flag for identifying "without latex" and "sterile product"
 producer article code
 batch
 expiry date
 other codes, if applicable, for example the code CIVAB (unique recognition system of a considerable part of the biomedical technologies present on the national market, usable in the entire process of acquisition and management of such goods) and codes pertaining to the sanitary goods (e.g. the code PARAF).

Advantages of the Finding

The process of tracking the sanitary goods and/or medical devices allows:
 greater uniformity of management between the various categories of devices and between the materials supplied by various companies,
 the pharmacist has information available due to which he can track the device up to the patient, hence with greater possibility to carry out compliance tests,
 an instrument for tracking in case of collection of signals in a structured manner of events (incident reporting) and in the case of signals by competent authorities with regard to problems on production batches, product withdrawal, various "alarms",
 greater possibility, due to the automatic support, to plan the provisioning,
 greater control for the situations of management in storage and in transit,
 optimized/automatic management of the expirations,
 possibility to introduce systems with facilitated management of surgical kits, due to the simultaneous reading of the various RFId tags, with important advantages with regard to the monitoring of the consumptions, for the correct attribution of the costs as well as for the optimization of the time dedicated by the operating room personnel for managing the devices.

In addition, with the creation of the containment structure/area and with the present tracking process, a very high level of tracking is actuated for the devices and goods treated, practically reducing to a minimum the operations that the operator must execute; the operator, both in the loading and unloading step, does not have to execute operations that are particularly different from those normally executed (for example, he does not have to press a button on the drawer where the device is positioned, or he does not have to report the operation, in the management software for the containment structure/area, nor is he involved with the passage of the device on a reader in the cabinet). Hence there are no risks, voluntary or involuntary, of skipping operations necessary for tracking the operation. All the operations are automatically tracked without any request for the operator to conduct particular activities apart from the simple placement of the device in the storage area or the collection of the same.

In addition, the tracking method is managed by a management software system, capable of automatically carrying out the operations of inventory, of expiry control, of stock management and request of new material, allowing a considerable time saving for the operators and reducing the risk of error in these procedures.

In addition, the management software system directly dialoguing with the information systems of the hospital/medical structure, can automatically transfer this information to other management systems (e.g. storage site, pharmacy, provisioning systems, management control systems).

Said objects and advantages are all attained by the structure (open and/or closed) for containing the sanitary goods provided with RFId tag and by the process for tracking and for the complete management of sanitary materials and goods and medical devices, object of the present finding, which is characterized for that provided for in the below-reported claims.

BRIEF DESCRIPTION OF THE FIGURES

These and other characteristics will be more evident from the following description of several embodiments illustrated as a mere non-limiting example in the enclosed drawing tables.

FIG. 1: a front view of a cabinet, panels open or structure for containing sanitary goods and/or materials and/or medical devices by means of RFID identification;

FIG. 2: the cabinet pursuant to FIG. 1, panels closed and security device,

FIG. 3: a containment area and/or structure for sanitary goods and/or medical devices by means of RFID identification.

DESCRIPTION OF THE FINDING

Method

The method that is the object of the finding is set for tracking sanitary materials and goods with RFId identification system, wherein said sanitary materials and goods are placeable and managed in an area arranged for storage.

Said area is prepared, or provided, with a plurality (P) of transceiving radio frequency identification antennae and associated connectivity devices; the plurality of antennae and connectivity devices are placed in a manner so as to receive and exchange information by means of RFId technology inside the set area, so as to record and detect the loading and/or collecting of the labeled materials and goods and exchange information relative to the identified objects.

The method provides for:

a. carrying out the exchange of tag-antenna information in a range of radiofrequencies comprised between 850 and 960 MHz (UHF)

b. restricting the range of radiofrequencies (UHF) through the shielding of the area arranged for storage of the materials and goods.

Specifically, said exchange of information in the radio frequency field (UHF) occurs by not turning on, at the same time, the plurality (P) of antennae arranged in the area set for the storage of the materials and goods. In other words, the method provides for exciting the tag of the materials and goods by means of a part of the antennae which form the plurality (P) provided inside the area, for cyclically varying, at time intervals, the turning on and off of said antennae.

In particular the turning on of the plurality (P) of antennae is of sequential type.

Alternatively, the turning on of the plurality (P) of antennae is of sequential and group type.

In detail, the exchange of information in the radio frequency field (UHF) occurs:

a. by creating, for each antenna turned on and arranged in the area, a series (M) of geometric configurations of the field, by means of a series of pointing directions that are different from each other, b. by creating, for each of the aforesaid configurations (M) or pointing directions, a series (N) of different polarizations of the electric field.

The set of the combinations (M×N), after the variation of the direction of the field and the polarity, are cyclically repeated.

Each of the combinations (M×N) is cyclically repeated according to a time interval (T).

The preferred configuration, with which the best tracking results are obtained, is that which applies seven geometric configurations of the field and four different polarizations of the electric field. The set of the twenty-eight combinations are cyclically repeated according to a time interval (T) comprised between forty and two-thousand milliseconds (during this time interval not all of the plurality (P) of antennae are simultaneously turned on).

Nevertheless, if the number of combinations was less than that indicated above, the time interval (T) could be greater than the reference interval.

Starting from the evidence that the antenna-tag system allows an improved detection if the two parts are found in relative movement with respect to each other, all the above-described expedients allow simulating this relative movement.

Below, the main characteristics are summarized of the technological and procedural solution.

The first aspect shown is the use of the UHF waves combined with the shielding of the zone containing objects to be tracked.

Secondly, another characteristic is that of the variability of the field generated inside the storage area.

This is obtained by providing for the use of dynamic transceiving antennae: even if fixed in points arranged inside the structure, the radiation diagram of said antennae shows a variety of pointing directions that are different from each other (multiple geometric configurations of the field). Each pointing direction is also enriched by different polarizations of the electric field. All possible configurations of the field are cyclically repeated in a manner such to obtain considerable advantages with respect to the conventional "static" antennae. A greater reliability is verified for reading the Tags, which can be arranged in a completely random manner, even quite close to each other (spaced only a few mm apart) and in a very high number (on the order of several hundred). In addition, the number of the antennae to be used drastically decreases, by a factor of ten, making the installation much simpler and sustainable and adaptable to various logistical and environmental situations.

The aforesaid variability of the field can be obtained (according to an embodiment variant illustrated in FIG. 1, last shelf on the bottom of the depicted cabinet) by arranging antennae within the shielded area, indicated with 13. Such antennae are movable by means of automatic actuation means or systems; the antennae 13 are moved inside the area (e.g. along slide guides) in order to strengthen the above-described effect and to obtain further advantages, such as:

greater possibility of success in detecting Tags, effective coverage of the entire storage volume, drastic reduction of the reading times, further reduction of the number of antennae used.

In general, also the movable antennae can in turn be of dynamic type, i.e. generating M×N combinations of direction and polarization.

The arrangement inside the storage area of fixed or movable antennae can even provide for the combination of both; some antennae will provide for varying the UHF field for the information exchange, others for varying the field itself and their polarity and at the same time provide that the remaining movable antennae are capable of being moved inside the area.

Any movement direction can be provided: linear or curvilinear, horizontal, vertical or oblique.

With regard to the configurability of the antennae, the finding provides, for each antenna, the possibility to configure the stay time on each configuration and the sequential nature of activation of the different configurations.

With regard to the arrangement of the antennae and the reading technique, it is emphasized that the antennae are arranged in a number and position in accordance with the reading area, in a manner so as ensure the coverage of the entire volume. The activation of the readers and the antennae is driven in a sequential manner: this prevents bottle necks and management problems of the data flows that the readers must manage.

Returning to the shielding of the containment area, the use of material with suitable RF shielding efficiency (aluminum) resolves known problems that up to now have prevented the use of such technology (UHF) for this application type, with the consequent obtainment of advantages with regard to quality of the detection of the Tags; such problems include:

emission problems, i.e. propagation of the RF electromagnetic field at distances greater than 11 m, with consequent possibility of reading Tags present in adjacent storage zones.

immunity problems: external sources could interfere with the correct functioning of the system, determining offset or partial readings of the Tags.

multiple reflections: the system results completely closed and shielded. This allows restricting the generated field inside the same. Due to the shielding, there will be the generation of multiple reflections of the RF field which, remaining confined within the reading area, will further strengthen the quality of the reading by increasing the probability of detection of the Tags, further reducing the reading time and the number of transceiving antennae necessary.

The finding allows attaining the objective of identifying, with a very high level of accuracy, all the devices contained in the managed storage zone, and to not detect any device that is situated outside the managed storage zone, independent of the number of tracked goods.

First Embodiment

The sanitary goods and medical devices (labeled with RFId tag) will be stored, at the wards/departments, within suitable closed structures or cabinets.

Also forming an object of the finding is the physical storage apparatus for the medical devices which are critical and provided with RFId tag.

With reference to FIG. 1, the cabinet 1 consists of a closed structure that can be opened by means of panels 5 and/or drawers and/or closure shutters/curtains, etc. . . . comprising therein shelves 4 (drawers) where sanitary goods 2 and/or medical devices 2 can be placed which have high criticality, to which RFId tag elements are applied, indicated with 6 on said device 2.

Each cabinet has integral therewith a plurality P of antennae 3 and connectivity devices arranged in a suitable manner, i.e. suitable for receiving and exchanging information according to the technologies and procedures described above, and secure inside the cabinet.

Through this structure, the management system is capable of detecting the loading and collecting of objects equipped with RFId tag, and to interact with the information system, in order to exchange information relative to the identified objects.

The cabinets can have controlled access, by means of locks 7 with electronic control: in such case, the enabled operators will be able to open the cabinet only upon recognition, attained with various possible modes (login, biometric systems, company electronic cards etc.). Each access will be recorded. Even loading and unloading of the devices will be automatically recorded, without the user having to insert the description of the device and the number of the collected and/or inserted quantities.

Upon closure of the cabinet, the inventory of the devices present therein will be carried out, updating types and quantities and possibly generating automatic reorder lists on the basis of the set low-stock levels.

The technology used and described above employs high-performance components, which allow a very quick reading of a high number of RFId tags, and also allow reading and distinguishing RFId tags localized very close to each other, and to not detect RFId tags positioned outside the area of interest.

From the structural standpoint, the solution is based on the use of modular elements that can be arranged as desired. The flexibility is useful for being adapted to the needs of the single wards/operating units. This modularity is assured by the possibility to configure the storage cabinet according to one's needs, in terms of height, width, type of closure panels and internal dividers. The structural modularity allows organizing the storage spaces in a manner so as to be adapted both to the environmental conditions where the cabinet is situated, and to the device type that one intends to store. Indeed, it is possible to create, for example, suitable housings for storing devices that must be positioned vertically, together with other devices that instead require drawers of various sizes. The cabinet type even allows storing, when convenient for the operators, packages that are not subjected to RFid labeling and hence not provided with automatic tracking.

Second Embodiment

The medical devices 2 labeled with RFId tag, indicated with 6, are directly stored at an area 8, for example one or more wards/departments, and more precisely within areas delimited by suitable separation barriers 9 (physical or not) and at least one RFId tag reading device. A series of antennae 3 and connectivity devices are positioned in a suitable manner in the area arranged for the storage of the labeled goods, within the set area or on the separation barriers. Through these devices, the management system is capable of detecting the introduction and collection of objects equipped with RFId tag, and to interact with the information system, in order to exchange information relative to the identified objects.

The technology used and described above employs high-performance components which allow a very quick reading of a high number of RFId tags, and also allow reading and distinguishing RFId tags localized very close to each other, and to not detect RFId tags positioned outside the area of interest.

The area can provide for a controlled access, in a manner such that only enabled operators can access it.

The introduction and collection of the devices labeled with RFId technology will be automatically recorded by the RFId tag reader, which will send all the information to suitable management software.

The user does not have to insert the description of the device and the number of the collected and/or introduced quantities.

After the operator has exited from the set area, the management system will command the completion of the inventory of the devices present therein, updating types and quantities and possibly generating automatic reorder lists on the basis of the set low-stock levels. The control and management system is thus static.

Third Embodiment

The medical devices, once labeled with label containing information stored on the RFId tag, are stored at the wards/departments
  within suitable areas/rooms delimited by suitable physical barriers;
  inside containment cabinets.

The aforesaid wards/departments containing the storage areas and/or the containment cabinets are provided with entry doors or accesses at which one or more RFId tag reading devices are associated.

Multiple series of antennae and connectivity devices are positioned in a manner so as to dynamically detect the access, by detecting and recording the passage of objects equipped with RFId tag and interacting with the information system, in order to exchange information relative to the identified objects.

If there are multiple RFId tag reading devices in series on the access, the flow of the object can be determined, identifying the inflow or outflow thereof.

The process completes the inventory of the devices present therein by updating types and quantities. Possibly, the process provides for generating automatic reorder lists on the basis of the set low-stock levels.

Devices with RFId tag may also possibly be arranged within the storage area.

The described process is directed in particular to the medical devices which have a certain criticality, from an economical standpoint due to high cost, with regard to the need to have a correct and protected preservation from the clinical-sanitary standpoint, and for the management in storage (which require the correct storage area size measurements).

This mode of identifying and tracking through RFId technology, capable of managing the passage through suitable passages, allows managing the procedural kits, i.e. variable sets of devices placed within suitable containers made of material compatible with the execution of the automatic readings of the RFId tags placed therein. In the management system, the unloading lists relative to the various procedural kits are pre-set. Thus, the management system knows the content of each kit and is therefore able to guide the operator in putting the kit together. Once the operator has constituted the kit, this is brought into the room where it will be used, passing through the automatic content identification passages/openings. Upon passage of the container into the passage/opening, before using the contents thereof in the specific clinical procedure (for example surgery operation, hemodynamic procedures, etc.), the content is identified and transmitted to the management information system. At the end of the clinical procedure, upon the subsequent passage into the passage/opening, the content is once again identified and transmitted to the management information system: from the difference between the two detected contents, the material used is identified and one proceeds with the suitable management operations (unloading of the material, reorder management, etc.).

The characteristics of the proposed method and system for managing and tracking can be summarized as follows:
- ease of use, since the automation practically does not oblige any operation of the personnel that is substantially different from the conventional management;
- controlled access, for protecting the access and identifying the operator who carries out the operations;
- modularity, with a consequent adaptability both to the environment in which they are positioned, and to the type of goods and devices that one intends to store;
- facilitated preparation, by the operators, of the procedural kits (e.g. surgical kits), and the correct loading and unloading of the materials that compose them;
- accuracy in identifying the RFId tags, and thus the devices, contained within the management area;
- protection from the detection of RFId tags, and hence devices, not belonging to the management area.

The present process can provide for, after the initials step of determining medical devices with high criticality, a step for labeling and encoding of the aforesaid identified medical devices, which occurs by applying a microchip on said device—such microchip containing the device data, and communication thereof is managed in radiofrequency; an antenna is also placed on said device. If the medical device has already been provided with said radio unit, there is no need for such step.

The process also allows managing the tracking of drug packages (applicable to very costly drugs or to preparations that enter into the operating room in order to complete the procedural kits, such as antibiotic treatment).

The invention claimed is:

1. A method for tracking sanitary materials and goods with an RFId identification system; said sanitary materials and goods provided with at least one label containing a microchip containing data of the material or good and an antenna; said sanitary materials and goods placeable in an area arranged for storage; said area being provided with a plurality (P) of transceiving radio frequency identification antennae and associated connectivity devices; said plurality (P) of transceiving radio frequency identification antennae and connectivity devices placed in a manner so as to receive and exchange information by means of RFId technology inside the area, so as to automatically record and detect the loading and/or collecting of the labeled materials and goods and exchange information relative to the identified objects, the method comprising:
- generating a variably radio frequency field (UHF) inside said area, said variably radio frequency field (UHF) being variable in both pointing direction and polarization of the electric field, wherein said plurality (P) of transceiving radio frequency identification antennae are dynamic transceiver antennae, such that each of said plurality (P) of transceiving radio frequency identification antennae has a radiation diagram with plural pointing directions, each pointing direction being enriched by different polarizations of the electric field;
- while generating the variably radio frequency field (UHF), carrying out the exchange of microchip-antenna information in a range of radio frequencies comprised between 850 and 960 MHz (UHF); and
- restricting the range of radio frequencies (UHF) by shielding the area arranged for storage of the materials and goods,
- wherein said exchange of microchip-antenna information occurs by not turning on, at the same time, the plurality (P) of transceiving radio frequency identification antennae arranged in the area,
- wherein the radio frequency field (UHF) varies inside said area and the exchange of information in the radio frequency field (UHF) occurs:
  a. by creating, for each of the plurality (P) of transceiving radio frequency identification antennae turned on and arranged in the area, a series (M) of geometric configurations of the field, by means of a series of the pointing directions that are different from each other, and
  b. by creating, for each of the geometric configurations of the field, a series (N) of different polarizations of the electric field, and
- wherein combinations of the geometric configurations and different polarizations (M×N), after the variation of the direction of the field and the polarity, are cyclically repeated over a period of time (T) during which not all of the plurality (P) of transceiving radio frequency identification antennae are simultaneously turned on.

2. The tracking method, according to claim 1, wherein said turning on of the plurality (P) of transceiving radio frequency identification antennae is of sequential, single or group type.

3. The tracking method, according to claim 1, further comprising varying the radio frequency field (UHF) by moving the plurality of transceiving radio frequency identification antennae within the area and wherein automatic actuation means or systems move the plurality of transceiving radio frequency identification antennae inside the area.

4. The tracking method, according to claim 1, further comprising exciting the microchip of the materials and goods by means of a part of the antennae which form the plurality (P) provided inside the area.

5. A closed structure that is openable and that comprises therein shelves for the sanitary goods and/or medical devices, an automatic actuation system, and the plurality of antennae and microchips, operating according to the method of claim 1, wherein the automatic actuation system operates to move at least one of the antennae in a horizontal direction along slide guides on one of shelves.

6. The closed structure according to claim 5, wherein the closed structure is a cabinet and the slide guides are provided on a last shelf on a bottom of the cabinet.

7. Area of a hospital/medical structure delimited by one or more barriers adapted to define an internal storage zone, comprising, in said zone or alternatively integral with said barriers, the plurality of antennae and microchips operating according to the method of claim 1.

8. Hospital/medical area delimited by one or more barriers adapted to define an internal storage zone, comprising entrance/exit doors or accesses equipped with RFId microchip reading devices; the plurality (P) of antennae, operating according to the method of claim 1, and connectivity devices positioned in a manner so as to control the access and record the passage of objects equipped with the microchips, and to interact with the information system, in order to exchange information relative to the identified objects.

9. The tracking method according to claim 1, the method being carried out in two or more of the areas, each managed by its own reader, the reading of the contents thereof being achieved by activating the various readers in a sequential manner or by groups.

10. The tracking method, according to claim 1, further comprising varying the radio frequency field (UHF) by having the plurality of antennae be a combination of fixed and movable antennae; some of the antennae will provide for varying the UHF field for the information exchange, by means of variation of the field itself and the polarity thereof, while the remaining antennae are movable inside the area; the movement direction of the movable antennae being linear or curvilinear, horizontal, vertical or oblique.

11. The tracking method, according to claim 10, further comprising generating M×N combinations of direction and polarization, also for the movable antennae.

\* \* \* \* \*